United States Patent
Murakami et al.

[11] Patent Number: 5,833,620
[45] Date of Patent: Nov. 10, 1998

[54] CONSTANT-RATE DEFLATOR FOR SPHYGMOMANOMETER

[75] Inventors: Tomomi Murakami; Hidetaka Tsuchiya; Masahiro Kasaya, all of Tanashi; Takanori Nakahara, Iida, all of Japan

[73] Assignee: Citizen Watch Co., Ltd., Tokyo, Japan

[21] Appl. No.: 737,459

[22] PCT Filed: Mar. 14, 1996

[86] PCT No.: PCT/JP96/00639

§ 371 Date: Nov. 14, 1996

§ 102(e) Date: Nov. 14, 1996

[87] PCT Pub. No.: WO96/28087

PCT Pub. Date: Sep. 19, 1996

[30] Foreign Application Priority Data

Mar. 15, 1995 [JP] Japan ................................. 7-055306

[51] Int. Cl.$^6$ ................................................. A61B 05/00
[52] U.S. Cl. .......................... 600/498; 137/504; 137/517
[58] Field of Search ................................ 137/504, 517; 600/498

[56] References Cited

U.S. PATENT DOCUMENTS

| | | | |
|---|---|---|---|
| 4,332,275 | 6/1982 | Brown | 137/504 |
| 4,497,323 | 2/1985 | Matsuura et al. | 600/498 |
| 4,708,166 | 11/1987 | Kobold | 137/517 |
| 5,220,925 | 6/1993 | Hishida | 600/498 |
| 5,301,713 | 4/1994 | Skoglund | 137/504 |

FOREIGN PATENT DOCUMENTS 1-158860  11/1989  Japan .

Primary Examiner—Robert L. Nasser
Attorney, Agent, or Firm—Kanesaka & Takeuchi

[57] ABSTRACT

A constant-rate deflator for constantly reducing air pressure of a cuff-type sphygmomanometer is disclosed. The constant-rate deflator includes a ventilation-adjusting shaft 2 with a truncate-cone recess 2a formed in one of the end thereof and a leak valve 1 with a hole 1b formed in the center thereof, the leak valve having a projection 1c opposing the recess of the ventilation-adjusting shaft and has the same truncated cone shape as the recess, wherein the rate of deflation is kept constant by adjusting the clearance between the projection of the leak valve and the recess of the ventilation-adjusting shaft.

8 Claims, 4 Drawing Sheets

CONSTANT-RATE DEFLATOR FOR SPHYGMOMANOMETER

BACKGROUND OF THE INVENTION

1. Field of the Invention

The present invention relates to a constant-rate deflator for a sphygmomanometer which reduces the air pressure in the pressurized chamber at a constant rate by gradually exhausting high pressure air in the chamber.

2. Description of the Background Art

In a cuff-type sphygmomanometer, the blood pressure is measured by identifying the pulsation phenomena (changes in the pulse pressure and the blood flow) caused during deflation of an inflated cuff. Therefore, a constant-rate deflator which gradually decreases the air pressure in the cuff depressing the arm, wrist, finger, and the like at a constant rate is used in the cuff-type sphygmomanometer.

Typical constant-rate deflators are proposed by Japanese Utility Model Application Laid-open No. 115507/1986, Japanese Patent Application Laid-open No. 193634/1986, and Japanese Patent Application Laid-open No. 193031/1991. These deflators are provided with a cylindrical tube in which the bottom is made from a flexible material such as rubber, with a slit being provided in a part thereof. To control the pressure decrease, the amount of opening of the slit is adjusted by providing a pressure from inside this cylindrical tube or from a side thereof by an indenter which is a component independent from the cylindrical tube.

Specifically, as shown in FIG. 6, a typical sphygmomanometer which is provided with a conventional constant-rate deflator has a high pressure chamber 50 directly joining with a cuff which depresses the arm, wrist, finger, and the like. This high pressure chamber 50 has a base plate 51 and an upper plate 52. Formed on a side of the base plate 51 is a lateral hole 51a, with steps, which is connected to an evacuation hole 60. A cylindrical ventilation valve 53 made of rubber is secured to this lateral hole 51a.

One or more slits 53a are provided at the circumferential surface on the bottom side of the cylindrical ventilation valve 53 along the longitudinal direction. These slits 53a are located in the high pressure chamber 50. On the other hand, an opening of the cylindrical ventilation valve 53 is positioned on the side of the ventilation hole 60 and secured by a securing ring 54.

Provided around the external circumference of the securing ring 54 is a male screw 54a which threadedly engages a female screw 60a formed around the internal circumference of the evacuation hole 60. The female screw 54b formed around the internal circumference is structured so as to be threadedly engaged by a male screw 55a which is formed around the external circumference of a head portion of an adjusting shaft 55. This adjusting shaft 55 has an evacuation hole 55b penetrating through the center thereof and a projection 55c having a size larger than the internal diameter of the cylindrical ventilation valve 53 at the tip.

The conventional constant-rate deflator with this configuration is operated as follows.

Specifically, the cylindrical ventilation valve 53 is placed in the lateral hole 51a which is formed on a side of the base plate 51 and secured by the securing ring screw 54. Then, the adjusting shaft 55 is threadedly engaged with the central female screw 54b of the securing ring screw 54, thereby causing the projection 55c at the tip to be inserted into the ventilation valve 53. Opening of the slit 53a provided in the ventilation valve 53 can be changed by changing the insertion distance of the projection 55c of the adjusting shaft 55 in this manner.

Here, the air in the high pressure chamber 50 is evacuated to the evacuation hole 55b of the adjusting shaft 55 through the slit 53a. At this instance, if the pressure of the high pressure chamber is high, the opening of the slit 53a of the ventilation valve 53 is decreased due to pressure at the external circumference, thereby decreasing the quantity of the exhaust gas and preventing the air to be evacuated in one stroke.

On the other hand, when the air pressure of the high pressure chamber 50 is low, the pressure to the slit 53a of the ventilation valve 53 at the external circumference is decreased, thereby expanding the opening of the slit 53a, resulting in an increase in the quantity of exhaust gas.

Therefore, the rate of pressure decrease in the high pressure chamber 50 is kept constant from a high-pressure state to a low-pressure state by the positional relationship of the tip projection 55c of the adjusting shaft 55 and the slit 53a of ventilation valve 53.

However, in the conventional constant-rate deflator shown in FIG. 6, because the opening of the slit 53a is adjusted by constantly pressing the cylindrical wall portion of the ventilation valve 53 with the tip projection 55c of the adjusting shaft 55, the cylindrical wall portion of the ventilation valve 53 is always kept in a pressurized state. In addition, because the ventilation valve 53 is made of a flexible material such as rubber, the material itself deteriorates over time so that the opening condition of the slit 53a is caused to change due to a so-called stress mitigation phenomenon. Thus, it is difficult to maintain the original opening condition first adjusted for a long period of time.

In addition, because the slit 53a of the ventilation valve 53 is formed by cutting with a tool like a cutter, it is also difficult to maintain the length of this slit 53a for a long time.

Because of these reasons, in the conventional constant-rate deflator the pressure cannot be reduced at a constant rate in a stable manner over an extended period of time. Errors may sometimes be produced in the measurement of blood pressure if such a sphygmomanometer is used over a long time.

Accordingly, an object of the present invention is to provide a constant-rate deflator for a sphygmomanometer capable of accurately measuring blood pressures in a stable manner over a long period of time while using a flexible material such as rubber.

DISCLOSURE OF THE INVENTION

The present invention provides a constant-rate deflator for reducing the air pressure of a cuff-type sphygmomanometer, comprising a ventilation-adjusting shaft having a recess formed on one end thereof and a ventilation valve having a hole formed at the center thereof and a projection having almost the same shape as that of the recess of the ventilation-adjusting shaft formed opposite the recess, wherein the rate of deflation is made constant by suitably adjusting the clearance between the projection of the ventilation valve and the recess of the ventilation-adjusting shaft.

According to the constant-rate deflator of the present invention having this configuration, there is no risk of deterioration of the leak valve, because there is no stress imposed on the leak valve while the sphygmomanometer is not being used. Therefore, the clearance between the projection of the leak valve and the recess of the ventilation-adjusting shaft, and the contact pressure can be maintained without change over a long period of time, ensuring deflation at a constant rate in a stable manner over a prolonged time period.

Moreover, in the present invention the recess of the ventilation-adjusting shaft valve and the projection of the leakage valve have the shape of a truncated cone. This ensures a stabilized change in the clearance between the projection and the recess according to the pressure change in the high pressure chamber during evacuation.

In addition, in the present invention at least one of the projection of the leak valve or the recess of the ventilation-adjusting shaft is provided with a projection and/or a groove. This configuration prevents defective peeling of the projection from the recess, thereby ensuring deflation at a constant rate.

DETAILED DESCRIPTION OF THE INVENTION AND PREFERRED EMBODIMENT

The present invention will be explained in detail by way of an embodiment of the present invention with reference to the drawings.

Figure 1:
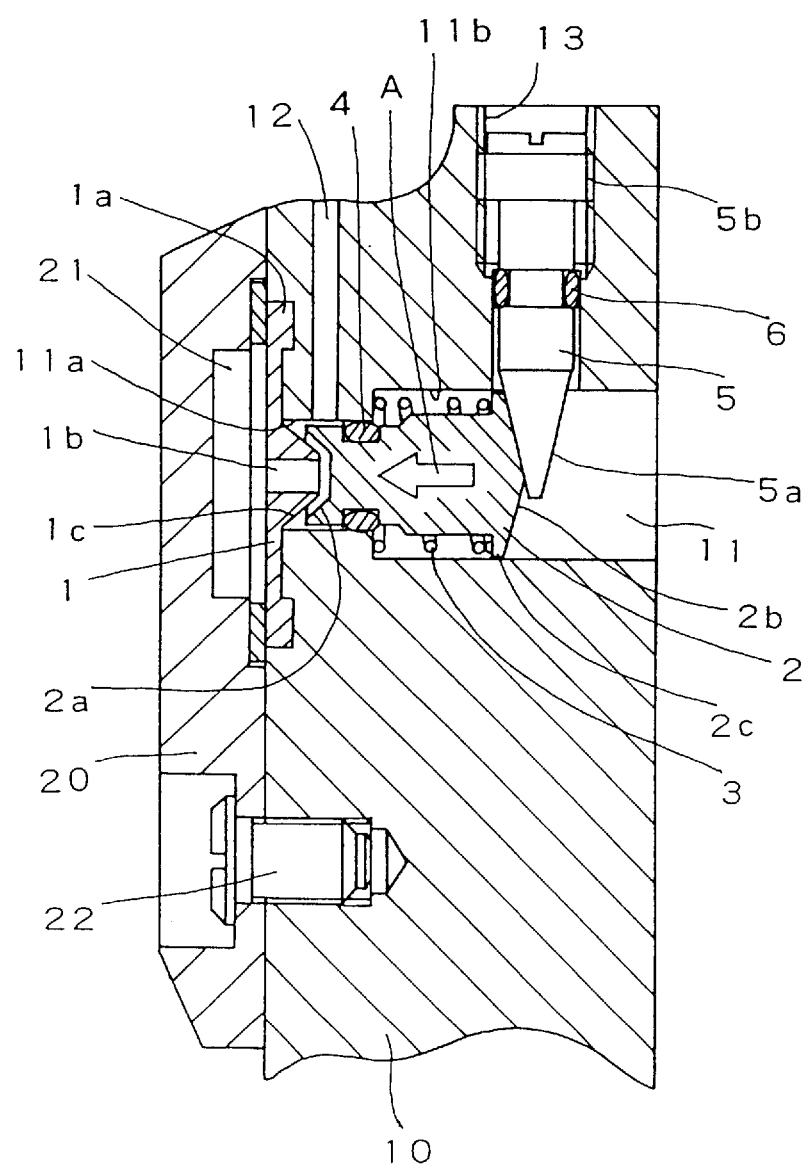
FIG. 1 is a sectional view of a first embodiment of the constant-rate deflator for a sphygmomanometer of the present invention.

FIG. 1 is a sectional view of the essential part of the first embodiment of the present invention.

In the constant-rate deflator of the sphygmomanometer of this first embodiment, the main body of the sphygmomanometer is formed of a base 10 and a cover 20.

The base 10 comprises a small-diameter part 11a and a large-diameter part 11b and is provided with a hole 11 for housing the ventilation-adjusting shaft along the vertical direction thereof.

On the other hand, provided on the cover 20 is a high pressure chamber 21 which is directly connected to a cuff for pressing the arm or wrist and to which air is fed from a pump (not shown in the drawing) of the sphygmomanometer. This cover 20 is placed on the surface of the base 10 secured by a screw 22, so that the high pressure chamber 21 is positioned above the aforementioned ventilation-adjusting shaft housing hole 11.

A pressure sensor of the sphygmomanometer is placed at a point where it is possible to detect the air pressure in the high pressure chamber 21, although this is not shown in the drawing.

A leak valve 1 is installed between the high pressure chamber 21 and the ventilation-adjusting shaft housing hole 11. This leakage valve 1 is formed from a soft material such as rubber or a soft plastic in a shape of a disk, with a circular projection 1a being provided around the external circumference to prevent leakage of air. Furthermore, provided in the center of the leak valve 1 is a hole 1b which joins the high pressure chamber 21 and the ventilation-adjusting shaft housing hole 11. A projection 1c is formed around the hole 1b in the shape of a truncated cone, projecting toward a ventilation-adjusting shaft 2 which is hereinafter discussed.

Housed in the hole 11 is a ventilation-adjusting shaft 2 which is made of a rigid material such as a metal or a hard plastic and is movable up and down in the vertical direction.

The diameter of this ventilation-adjusting shaft 2 in the part corresponding to the above-described small-diameter part 11a of the ventilation-adjusting shaft housing hole 11 is sufficiently large to allow a leak space to be formed between the ventilation-adjusting shaft 2 and the small-diameter part 11a. The diameter in the part corresponding to the above-described large-diameter part 11b is sufficiently large to allow a coil spring 3 to be placed between the ventilation-adjusting shaft 2 and a wall of the large-diameter part 11b.

Formed on one end of the ventilation-adjusting shaft 2 opposing the leak valve 1 is a recess 2a having the same truncate cone shape as that of the projection 1c of the leak valve 1. Formed on the other end of the ventilation-adjusting shaft 2 is a conical projection 2b which is connected to a later-described second adjusting shaft 5. A flange 2c with a diameter larger than the large-diameter part of the ventilation-adjusting shaft 2 is formed around the circumference of the projection 2b.

The coil spring 3 is provided around the external circumference of the ventilation-adjusting shaft 2. This coil spring is positioned between the wall of the stepped large diameter part. 11b of the ventilation-adjusting shaft housing hole 11 and the flange 2c of the ventilation-adjusting shaft 2, constantly pressing the ventilation-adjusting shaft 2 in the direction opposite to the leakage valve 1.

In addition, an O-ring 4 is provided around the external circumference of the ventilation-adjusting shaft 2 in the position corresponding to the small-diameter part 11a of the cylindrical housing hole 11 for the ventilation-adjusting shaft 2, so as to ensure a smooth up-and-down movement of the shaft 2.

A second adjusting shaft 5 is housed in a second adjusting shaft housing hole 13 which is provided so as to cross at right angles the large-diameter part 11b of the ventilation-adjusting shaft housing hole 11. This second adjusting shaft 5 possesses at its end a tapered part 5a which comes in contact with the conical projection 2b at the other end of the above-mentioned ventilation-adjusting shaft 2 and, at the other end, is provided with a screw part 5b on which a male screw is formed, the male screw threadedly engaging a female screw formed around the internal surface of the second adjusting shaft housing hole 13.

An O-ring is provided between the tapered part 5a of the second adjusting shaft 5 and the screw part 5b to ensure smooth rotation of the second adjusting shaft 5.

The constant-rate deflator of the first embodiment having the above-mentioned configuration is operated as follows.

When the ventilation-adjusting shaft 2 is caused to advance within the ventilation-adjusting shaft housing hole 11 by rotating the screw 5b of the second adjusting shaft 5 using a screw driver, the ventilation-adjusting shaft 2 is caused to move in the direction indicated by the arrow A against the force of the coiled spring 3 by the tapered part 5a at the end of the second adjusting shaft 5. In contrast, if the screw 5b of the second adjusting shaft 5 is rotated in the reverse direction by a screw driver, thereby causing the second adjusting shaft 2 to move away from the ventilation-adjusting shaft housing hole 11, the ventilation-adjusting shaft 2 is moved in the direction opposite to the direction indicated by the arrow A, by the force of the coiled spring 3.

The clearance between the truncated cone recess 2a at one end of the ventilation-adjusting shaft 2 and the projection 1c in the shape of a truncate cone of the leak valve 1, and the contact pressure in these parts, are adjusted by causing the ventilation-adjusting shaft 2 to move in the vertical direction.

Here, the clearance between the projection 1c of the leak valve 1 and the recess 2a of the ventilation-adjusting shaft 2 is adjusted so that when air is fed to the cuff from a pump, the projection 1c is displaced toward the recess 2a, thereby causing the projection 1c and the recess 2a to come in contact, whereas when the supply of air to the cuff is halted, there is a clearance between these parts to an extent sufficient to allow constant deflation during a specified period of time.

The constant deflation occurs as follows. Specifically, air is fed to the cuff by a pump until the air pressure in the high pressure chamber 21 reaches a specified pressure. Then, the supply of air from the pump is halted and the air pressure in the high pressure chamber 21 is maintained at a specified level. At this time, the leak valve 1 is deformed by the air pressure to the side of the ventilation-adjusting shaft 2, whereby the projection 1c of the leak valve 1 is caused to move to the side of the recess 2a at the end of the ventilation-adjusting shaft 2. The clearance between the projection 1c of the leakage valve 1 and the recess 2a of the ventilation-adjusting shaft 2 is decreased in this manner.

Accordingly, the high pressure air is passed through a hole 1b provided for exhausting air in the center of the leak valve 1, a narrow clearance between the recess 2a at the end of the ventilation-adjusting shaft 2 and the projection 1c of the leak valve 1, a leak space between the small-diameter part 11a of the ventilation-adjusting shaft 2 and the ventilation-adjusting shaft housing hole 11, and is exhausted from the exhaust gas hole 12 of the base 10. When the air pressure in the high pressure chamber is decreased by exhaustion of the gas in this manner, deformation of the leak valve 1 is also decreased, thereby expanding the clearance between the recess 2a at the end of the ventilation-adjusting shaft 2 and the projection 1c of the leak valve 1. This ensures that the air is easily exhausted even though the pressure is low. As a result, the air in the high pressure chamber 21 is exhausted at a constant rate irrespective of the air pressure, and deflation at a constant rate is ensured.

In this instance, the flange part 1a of the leak valve 1 adheres to the surface of the base 10 from the time when the air pressure is high until the air pressure becomes low, thereby preventing leakage of the air.

Because the second adjusting shaft 5 is arranged at right angles with the ventilation-adjusting shaft 2 in the constant-rate deflator of the above-mentioned first embodiment, the whole configuration of the sphygmomanometer can be made thin. Accordingly, this constant-rate deflator is suitable for use in a wrist watch type sphygmomanometer.

Figure 2:
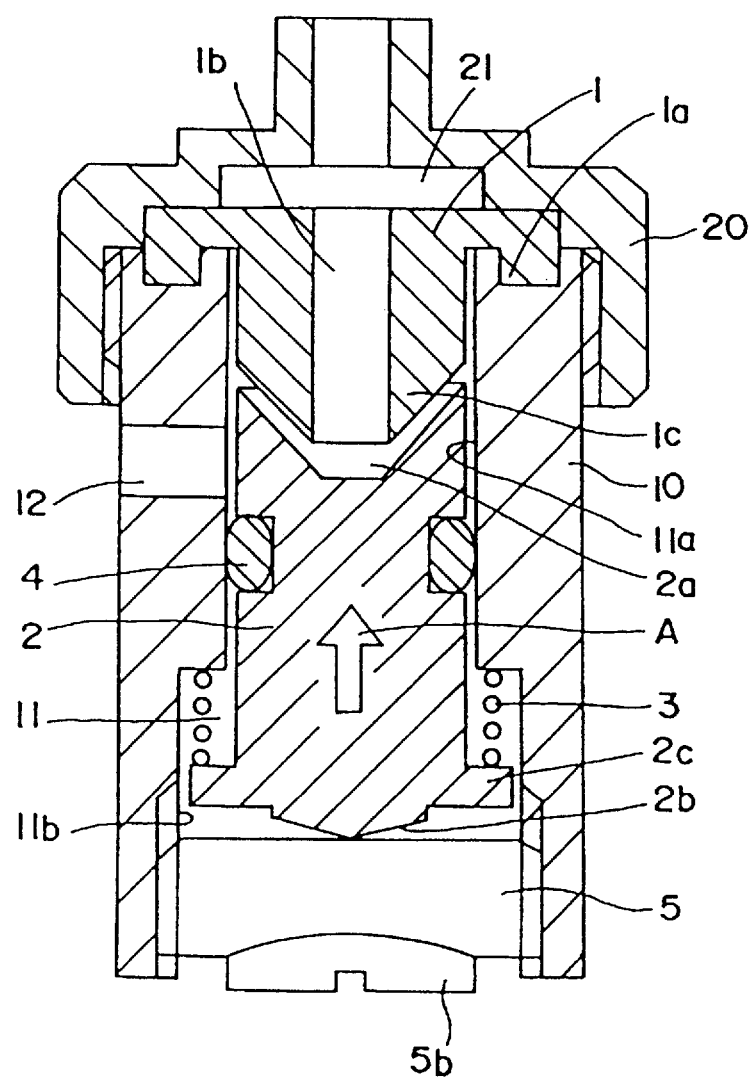
FIG. 2 is a sectional view of a second embodiment of the constant-rate deflator for a sphygmomanometer of the present invention.

FIG. 2 is a sectional view showing the main part of the second embodiment of the present invention.

The constant-rate deflator of this second embodiment is different from the constant-rate deflator of the first embodiment in that in this second embodiment the cover 10 threadedly engage the base 20 in its entirety and the second adjusting shaft 5 is arranged in the lower part of the ventilation-adjusting shaft 2 coaxially therewith. Accordingly, the clearance between the projection 1c of the leakage valve 1 and the recess 2a at the end of the ventilation-adjusting shaft 2 is adjusted in this constant-rate deflator of the second embodiment by rotating the screw part 5b using a screw driver from the lower part of the base 20, thereby causing the second adjusting shaft 5 to move back and forth.

Figure 3A:
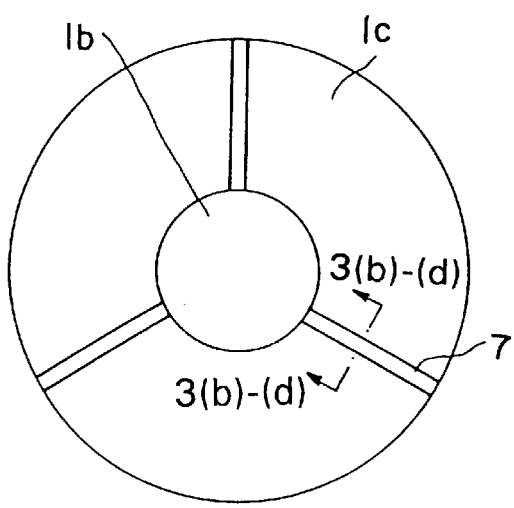
FIG. 3(a) is a view from the bottom of the projection of the leak valve and FIGS. 3(b), 3(c), and 3(d) are sectional views along lines 3(b)–(d) and 3(b)–3(d) in FIG. 3(a).
Figure 3B:
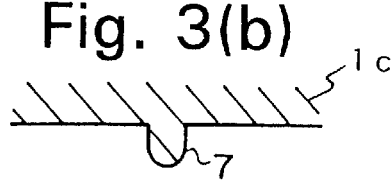
Figure 3C:
Figure 3D:
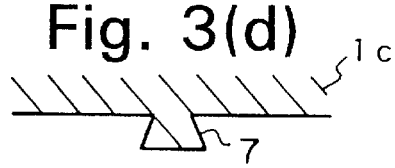
Figure 4A:
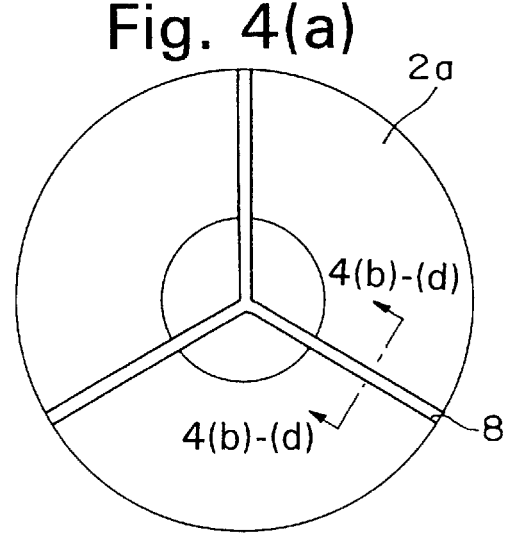
FIG. 4(a) is a view from the top of the recess of the ventilation-adjusting shaft and FIGS. 4(b), 4(c), and 4(d) are sectional views along the line 4(b)–(d) and 4(b)–4(d)in FIG. 4(a).

FIG. 3 and FIG. 4 show the third embodiment of the present invention, wherein FIG. 3(a) shows a projection of the leak valve viewed from the bottom and FIG. 4(a) is a recess of the ventilation-adjusting shaft viewed from the top.

In this embodiment, a protrusion is formed on the surface of the projection of the leak valve and a groove is formed on the surface of the recess of the ventilation-adjusting shaft. Specifically, when air is fed to the cuff by a pump for measuring blood pressure, the air pressure in the high pressure chamber 21 instantaneously increases and the projection 1c of the leak valve 1 is caused to move significantly so that the projection 1c comes in contact with and applies pressure to the recess 2a of the ventilation-adjusting shaft 2. In this instance, if the surface of the projection 1c and the surface of the recess 2a come closely in contact with each other, there is a case where the projection 1c and the recess 2a do not separate even if the air supply to the cuff is halted. This hinders smooth exhaustion of air and thus constant deflation, making it difficult to accurately measure the blood pressure.

Therefore, in order to ensure that a clearance is produced between 1c and 2a without fail even if the projection 1c of the leak valve 1 moves during air supply to the cuff so as to press against the recess 2a of the ventilation-adjusting shaft 2, protrusions 7 are formed on the projection 1c of the leak valve 1 or grooves 8 are formed in the recess 2a of the ventilation-adjusting shaft 2.

Specifically, as shown in FIG. 3(a), several protrusions 7 are radially formed from the hole 1b in the center of the projection 1c of the leak valve 1. These protrusions 7 may have a U-shaped cross-section as shown in FIG. 3(b), a rectangular cross-section as shown in FIG. 3(c), or an inverted trapezoid cross-section as shown in FIG. 3(d). These configurations are effective for preventing the protrusions 7 from being crushed when the projection 1c of the leak valve 1 comes in contact with and applies pressure to the recess 2a of the ventilation-adjusting shaft 2.

Figure 4B:
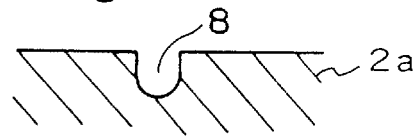
Figure 4C:
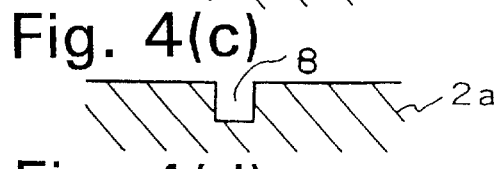
Figure 4D:

Furthermore, as shown in FIG. 4(a), several grooves 8 are radially formed from the center of the recess 2a of the ventilation-adjusting shaft 2. The cross-section of the grooves can also be made in a U-shaped configuration of as shown in FIG. 4(b), rectangular as shown in FIG. 4(d), or trapezoid as shown in FIG. 4(d), for preventing the grooves 8 from being crushed when the projection 1c of the leak valve 1 presses against the recess 2a of the ventilation-adjusting shaft 2.

Because both the protrusions 7 and the grooves 8 are provided for the purpose of easily parting the projection 1c of the leak valve 1 from the recess 2a of the ventilation-adjusting shaft 2 during constant deflation, their width and height (depth) may be small. For example, in the case where three protrusions 7 and three grooves 8 are formed, their width may be several tens of microns and their height (depth) may be several microns.

Figure 5:
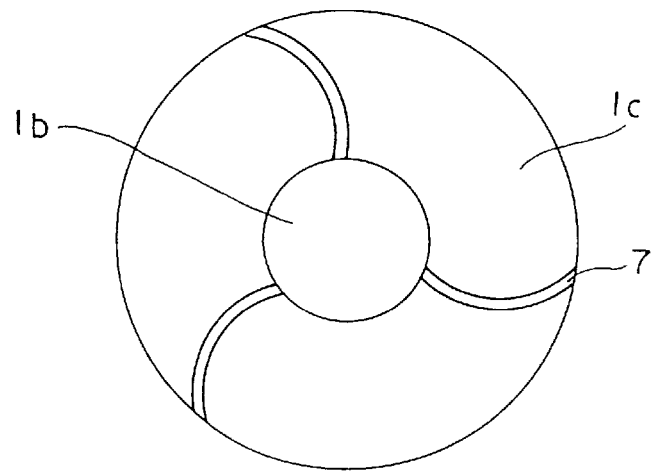
FIG. 5. is a drawing corresponding FIG. 3(a), showing another method of arranging the protrusions.
Figure 6:
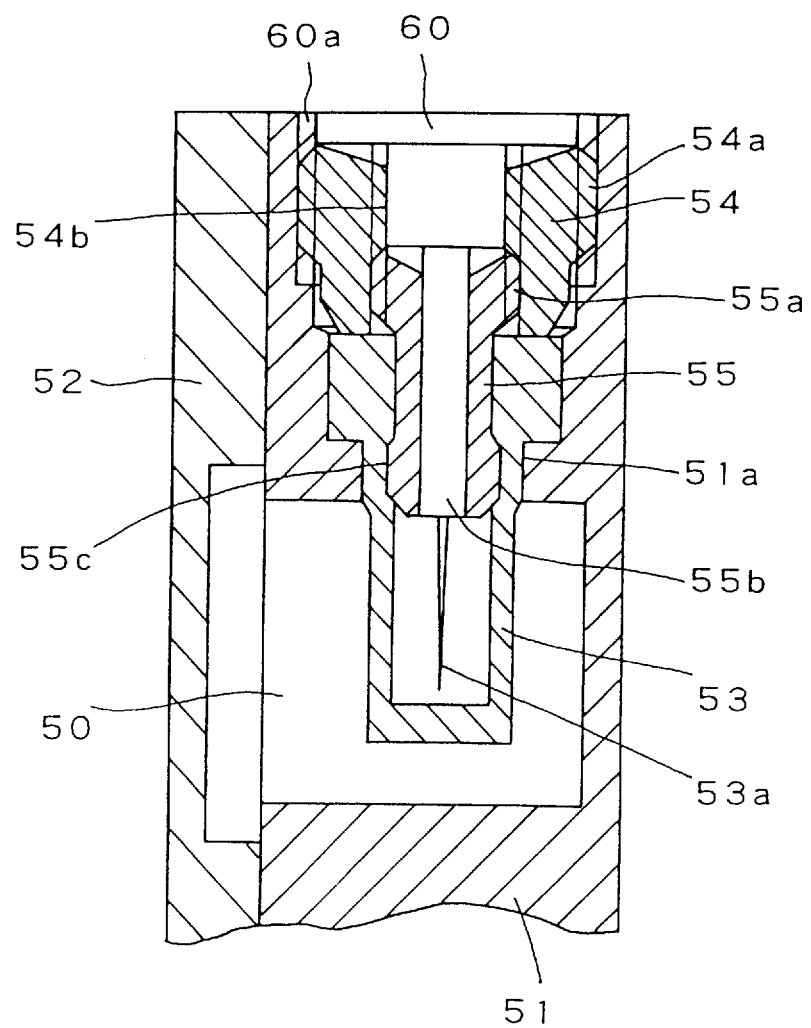
FIG. 6 is a sectional view of a constant-rate deflator for a conventional sphygmomanometer.

The locations where the protrusions 7 and the grooves 8 are provided are not necessarily limited to those shown in FIG. 3(a) or FIG. 4(a). Various methods of locating these protrusions 7 and the grooves 8 other than those shown in these figures are conceivable, for example, it is possible to have curved protrusions 7 and grooves 8 as shown in FIG. 5.

Moreover, it is possible to form the protrusions 7 on the recess 2a of the ventilation-adjusting shaft 2, and the grooves 8 on the projection 1c of the leak valve 1. It is also possible to provide these combination on both the recess 2a and the opposing projection 1c.

INDUSTRIAL APPLICABILITY

This constant-rate deflator can be applied to various cuff-type sphygmomanometers.

What is claimed is:

1. A constant-rate deflator for constantly reducing air pressure in a cuff of a sphygmomanometer, comprising:

a base having a housing hole, a ventilation hole communicating with the housing hole, and a high pressure chamber communicating with the housing hole, a ventilation-adjusting shaft slidably situated in the housing hole and having a recess at one side close to the ventilation hole, and a leak valve deformably situated between the high pressure chamber and the housing hole, said leak valve having a center hole in a center thereof, and a projection formed around the center hole with a shape substantially same as that of the recess of the ventilation-adjusting shaft and facing the recess to thereby form a space as a flow path between the projection of the leak valve and the recess of the ventilation-adjusting shaft, a rate of deflation of air pressure from the high pressure chamber to the ventilation hole being kept constant by adjusting said space.

2. The constant-rate deflator according to claim 1, further comprising a second adjusting shaft situated in the base to contact the ventilation-adjusting shaft, said second adjusting shaft adjusting the space between the projection of the leak valve and the recess of the ventilation-adjusting shaft.

3. The constant-rate deflator according to claim 2, wherein the second adjusting shaft is installed in a direction crossing at right angles with the ventilation-adjusting shaft.

4. The constant-rate deflator according to claim 2, further comprising a spring situated in the base to urge the ventilation-adjusting shaft in a direction away from the leak valve.

5. The constant rate deflator according to claim 2, wherein said ventilation-adjusting shaft includes an inclined surface at a side opposite to the recess, said second adjusting shaft having a tapered part contacting the inclined surface.

6. The constant rate deflator according to claim 1, wherein said leak valve is attached to the base such that when no pressure is formed in the high pressure chamber, no pressure is applied to the leak valve.

7. The constant-rate deflator according to claim 1, wherein the projection of the leak valve and the recess of the ventilation-adjusting have the shape of a truncated cone.

8. The constant-rate deflator according to claim 1, wherein at least one of the projection of the leak valve and the recess of the ventilation-adjusting shaft is provided with protrusions or grooves, or both.

* * * * *